United States Patent [19]
Skubitz et al.

[11] Patent Number: 5,703,205
[45] Date of Patent: *Dec. 30, 1997

[54] LAMININ A CHAIN POLYPEPTIDES FROM THE AMINO TERMINAL GOLBULAR DOMAIN

[75] Inventors: Amy P. N. Skubitz; Leo T. Furcht, both of Minneapolis, Minn.

[73] Assignee: Regents of the University of Minnesota, Minneapolis, Minn.

[*] Notice: The term of this patent shall not extend beyond the expiration date of Pat. No. 5,276,136.

[21] Appl. No.: 72,283

[22] Filed: Jun. 7, 1993

Related U.S. Application Data

[63] Continuation of Ser. No. 895,252, Jun. 8, 1992, Pat. No. 5,276,136, which is a continuation of Ser. No. 646,291, Jan. 25, 1991, abandoned.

[51] Int. Cl.$^6$ .............. A61K 38/00; C07K 7/00; C07K 7/10; C07K 7/06
[52] U.S. Cl. .............. 530/324; 530/326; 530/327; 530/330; 514/12; 514/13
[58] Field of Search .............. 530/326, 324, 530/327; 514/14, 13, 12

[56] References Cited

U.S. PATENT DOCUMENTS

| | | | |
|---|---|---|---|
| 4,565,789 | 1/1986 | Liotta et al. | 436/504 |
| 4,870,160 | 9/1989 | Charonis et al. | 530/326 |
| 4,876,332 | 10/1989 | Tsilibary et al. | 530/326 |

FOREIGN PATENT DOCUMENTS

| | | |
|---|---|---|
| 00211152 | 7/1981 | European Pat. Off. . |
| 0244688 A2 | 11/1987 | European Pat. Off. . |

OTHER PUBLICATIONS

Sasaki, et al, "Laminin, a Multidomain Protein", J. Biol. Chem. vol. 263, (32) 1988, pp. 16536–16544.
D. Grant et al., "Two Different Laminin Domains Mediate the Differentiation of Human Endothelial Cells into Capillary-like Structures in Vitro", *Cell*, 58, 933–943 (1989).
J. Graff et al., "Identification of an Amino Acid Sequence in Laminin Mediating Cell Attachment, Chemotaxis, and Receptor Binding", *Cell*, 48, 989–996 (1987).
J. Sanes et al., *J. Cell Biol.*, 111, 1685 (1990).
D. Kirchhofer et al., *J. of Biol. Chemistry*, 265, 615 (1990).
R. Kremer et al. *J. Cell Biol.*, 111, 1233 (1990).
D. Hall et al., *J. Cell Biol.*, 110, 2175 (1990).
A. Sonnenberg et al., *J. Cell Biol.*, 110, 2145 (1990).
J. Schittny and P. Yurchenco, *J. Cell Biol.*, 110, 825 (1990).
M. Bruch et al., *Eur. J. Biochem.*, 185, 271 (1989).
K. Gehlsen et al., *J. Biol. Chem.*, 264, 19034 (1989).
T. Herbst et al., *J. Cell Biol.*, 106, 1365 (1988).
Y. Christiane et al., *Chemical Abstracts*, 109, 398, No 108013q (1988).
R. Okazaki et al., *Chemnical Abstracts*, 109, 488, No. 522615t (1988).
L. Hartl et al., *Chemical Abstracts*, 109, 258, No. 19085x (1988).
Y. Iwamoto et al., *Chemical Abstracts*, 109, 444, No. 4628c (1988).
Y. Iwamoto et al., *Chemical Abstracts*, 108, 29, No. 68408t (1988).
M. Sasaki et al., *PNAS*, 84, 935 (1987).
J. Graf et al., *Biochemistry*, 26, 6896 (1987).

(List continued on next page.)

*Primary Examiner*—Cecilia J. Tsang
*Assistant Examiner*—S. Marshall
*Attorney, Agent, or Firm*—Merchant, Gould, Smith, Edell, Welter & Schmidt

[57] ABSTRACT

Polypeptides derived from domain VI of the amino terminal globule of the A chain of laminin and having sequences of at least about 5 amino acids, and which exhibit cell adhesion and cell spreading capacity are described.

Medical devices such as prosthetic implants, per-cutaneous devices and cell culture substrates coated with a composition including the described polypeptides are also provided.

1 Claim, 11 Drawing Sheets

OTHER PUBLICATIONS

M. Sasaki et al., *Chemical Abstracts*, 107, 292, No. 193110v (1987).
R. Timpl and M. Dziadek, *International Review of Exper. Pathology*, 29, 1 (1986).
G. Laurie et al., *J. Mol. Biol.*, 189, 205 (1986).
A. Charonis et al., *J. Cell Biiol.*, 103, 1689 (1986).
P. Yurchenco et al. *J. of Biol. Chem.*, 260, 7636 (1985).
D. roberts et al., *PNAS*, 82, 1306 (1985).
A. Hrwitz et al., *J. Cell Biol.*, 101, 2134 (1985).
J. McCarthy et al., *Cancer and Metastasis Reviews*, 4, 125 (1985).
L. Furcht et al., *Biochemistry and Molecular Genetics of Cancer Metastasis*, K. Lapis et al., eds., Martinus Nijhoff (1985).
A. Charonis et al., *J. Cell Biol.*, 100, 1848 (1985).
P. Liesi et al., *Chemical Abstracts*, 105, 454, No. 22265d (1985).
L. Liotta, *Am. J. Path.*, 117, 339 (1984).
D. Edgar et al., *EMBO Journal*, 3, 1463 (1984).
V. Terranova et al., *PNAS*, 80, 444 (1983).
D. Kennedy et al., *J. Cell. Physio.*, 114, 257 (1983).
H. Malinoff and M. Wicha, *J. Cell Biol.*, 96, 1475 (1983).
H. Lesot et al., *EMBO Journal*, 6, 861 (1983).
R. Timpl et al., *J. Biol. Chem.*, 258, 8922 (1983).
C. Howe et al., *Chemical Abstracts*, 99, 249, No. 66173j (1983).
U. Ott et al., *Eur. J. Biochem.*, 123, 63 (1982).
J. Kyte and R. Doolittle, *J. Mol. Biol.*, 157, 105 (1982).
P. Ekblom, *J. Cell Biol.*, 91, 1 (1981).
J. Engel et al., *J. Mol. Biol.*, 150, 97 (1981).
R. Timpl and H. Rohde, *J. Biol. Chem.*, 254, 9933 (1979).

LAMININ A CHAIN POLYPEPTIDES FROM THE AMINO TERMINAL GOLBULAR DOMAIN

This is a continuation of application Ser. No. 07/895,252, filed Jun. 8, 1992, now U.S. Pat. No. 5,276,136 which is a continuation of application Ser. No. 07/646,291, filed Jan. 25, 1991, now abandoned.

GOVERNMENT SUPPORT

This invention was made with government support under contract No. CA-29995 by the U.S. National Institutes of Health. The government has certain rights in the invention.

BACKGROUND OF THE INVENTION

The adhesion of mammalian cells to the extra-cellular matrix is of fundamental importance in regulating growth, adhesion, motility and the development of the proper cellular phenotype. This has implications for normal cell growth and development, wound healing, chronic inflammatory diseases, diabetes, and tumor metastasis. Evidence accumulated over the last several years suggests that the molecular basis for the adhesion of both normal and transformed or malignant cells is complex and probably involves several distinct cell surface molecules. Extracellular matrices consist of three types of macromolecules: collagenous glycoproteins, proteoglycans and noncollagenous glycoproteins.

One noncollagenous adhesive glycoprotein of interest is laminin. Laminin likely is one of a multigene family of related molecules [Ohno et al., *Conn. Tiss. Res.*, 15, 199–207 (1986); Hunter et al., *Nature*, 338, 229–234 (1989); Sanes et al., *J. Cell Biol.*, 111, 1685–1699 (1990)]. Laminin is a high molecular weight (approximately 850,000; from the mouse Engelbreth-Holm-Swarm tumor) extracellular matrix glycoprotein found almost exclusively in basement membranes. [Timpl et al., *J. Biol. Chem.*, 254, 9933–9937 (1979)]. Basement membranes are an ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation, and differentiation, while migratory cells, both normal and neoplastic, must traverse the basement membrane in moving from one tissue to another.

Laminin isolated from the Engelbreth-Holm-Swarm murine tumor consists of three different polypeptide chains: B1 with 215,000 MW, B2 with 205,000 MW and A with 400,000 MW [Timpl and Dziadek, *Intern. Rev. Exp. Path.*, 29, 1–112 (1986)]. When examined at the electron microscopic level with the technique of rotary shadowing, it appears as an asymmetric cross, with three short arms 37 nm long {the lateral short arms having two globular domains and the upper short arm having three globular domains [Sasaki et al., *J. Biol. Chem.*, 263, 16536–16544 (1988)]}, and one long arm 77 nm long, exhibiting a large terminal globular domain [Engel et al., *J. Mol. Biol.*, 150, 97–120 (1981)]. The three chains are associated via disulfide and other chemical bonds. Structural data shows that laminin is a very complex and multidomain protein with unique functions present in specific domains.

Laminin is a major component of basement membranes and is involved in many functions. Laminin has the ability to bind to other basement membrane macromolecules and therefore contributes to the structural and perhaps functional characteristics of basement membranes.

Laminin promotes the adhesion and spreading of a multitude of cells and binds a variety of proteoglycans [Timpl and Dziadek, supr$_a$ (1986)]. Studies utilizing enzymatic digests of laminin or monoclonal antibodies raised against laminin have defined some of the biologically active regions of the 400 kD A chain of laminin. The amino terminal globular domain at the top of the molecule is involved in laminin-laminin self assembly [Yurchenco et al., *J. Biol. Chem.*, 260, 7636–7644 (1985)] and the adhesion of hepatocytes [Timpl et al., *J. Biol. Chem.*, 255, 8922–8927 (1983)]. In addition, its large carboxy-terminal globular domain binds heparin [Ott et al., *Eur. J. Biochem.*, 123, 63–72 (1982); Skubitz et al., *J. Biol. Chem.*, 263, 4861–4868 (1988)], while neurite cell outgrowth and cell adhesion is localized to the region directly above this globule [Edgar et al., *EMBO J.*, 3, 1463–1468 (1984); Engvall et al., *J. Cell Biol.*, 103, 2457–2465 (1986); Goodman et al., *J. Cell Biol.*, 105, 589–598 (1987)].

Another important feature of laminin is its ability to associate with cell surface molecular receptors and consequently modify cellular phenotype in various ways. Receptors for laminin ranging in molecular size from 55 to 180 kD have been isolated from a variety of normal and malignant cell lines [Rao et al., *Biochem. Biophys. Res. Commun.*, 111, 804–808 (1983); Lesot et al., *EMBO J.*, 2, 861–865 (1983); Malinoff and Wicha, *J. Cell Biol.*, 96, 1475–1479 (1983); Terranova et al., *Proc. Natl. Acad. Sci. U.S.A.*, 80, 444–448 (1983); Barsky et al., *Breast Cancer Res. Treat.*, 4, 181–188 (1984); von der Mark and Kühl, *Biochim. Biophys. Acta.*, 823, 147–160 (1985); Wewer et al., *Proc. Natl. Acad. Sci. U.S.A.*, 83, 7137–7141 (1986); Hinek et al., *J. Cell Biol.*, 105, 138a (1987); Yoon et al., *J. Immunol.*, 138, 259–265 (1987); Smalheiser and Schwartz, *Proc. Natl. Acad. Sci. U.S.A.*, 84, 6457–6461 (1987); Yannariello-Brown et al., *J. Cell Biol.*, 106, 1773–1786 (1988); Mercurio and Shaw, *J. Cell Biol.*, 107, 1873–1880 (1988); Kleinman et al., *Proc. Natl. Acad. Sci. U.S.A.*, 85, 1282–1286 (1988); Hall et al., *J. Cell Biol.*, 107, 687–697 (1988); Clegg et al., *J. Cell Biol.*, 107, 699–705 (1988)]. In the case of human glioblastoma cells [Gehlsen et al., *Science*, 241, 1228–1229 (1988)], several chicken cell types [Horwitz et al., *J. Cell Biol.*, 101, 2134–2144 (1985)], platelets [Sonnenberg et al., *Nature*, 336, 487–489 (1988)], and neuronal cell line PC12 [Tomaselli et al., *J. Cell. Biol.*, 105, 2347–2358 (1987); and *J. Cell Biol.*, 107, 1241–1252 (1988)], the laminin receptor was determined to be an integrin. To date, however, the exact sequence of amino acid residues of laminin to which most of these receptors bind is unknown.

Recently, the amino acid sequences of the B1, B2, and A chains of laminin have been determined [Barlow et al., *EMBO J.*, 3, 2355–2362 (1984); Sasaki et al., *Proc. Natl. Acad. Sci. U.S.A.*, 84, 935–939 (1987); Sasaki et al., *J. Biol. Chem.*, 263, 16536–16544 (1988); Sasaki and Yamada, *J. Biol. Chem.*, 262, 17111–17117 (1987); Pikkarainen et al., *J. Biol. Chem.*, 262, 10454–10462 (1987); Pikkarainen et al., *J. Biol. Chem.*, 263, 6751–6758 (1988); Hartl et al., *Eur. J. Biochem.*, 173, 629–635 (1988)], allowing peptides to be synthesized from domains of laminin with reported functional activity. Three peptides have been synthesized from the B1 chain of laminin which promote cell adhesion. The first peptide, cys-asp-pro-gly-tyr-iso-gly-ser-arg (SEQ ID NO:6), located near the intersection of the cross, promotes the adhesion of a variety of cells [Graf et al., *Cell*, 48, 989–996 (1987a); *Biochemistry*, 26, 6896–6900 (1987b)] and is tought to bind a 67 kD protein laminin receptor [Graf et al., supra (1987b); Wewer et al., supra (1986)]. The second, peptide F-9 (arg-tyr-val-val-leu-pro- arg-pro-valcys-phe-glu-lys-gly-met-asn-tyr-thr-val-arg) (SEQ ID NO:7), also promotes the adhesion of a varietyof cells and binds heparin (U.S. Pat. No. 4,870,160) Charonis et al. *J. Cell Biol.*, 107, 1253–1260 (1988). A third peptide from the B1 chain of laminin, termed AC15 {arg-ile-gln-asn-leu-leu-lys- ile-thr-asn-leu-arg-ile-lys-phe-val-lys (SEQ ID NO:8) [Kouzi-Koliakos et al., *J. Biol. Chem.*, 264, 17971–17978 (1989)]} also binds heparin, and is derived from the outer globule of a lateral short arm. AC15 promotes the adhesion of murine melanoma and bovine aortic endothelial cells [Koliakos et al., *J. Cell Biol.*, 109, 200a (1989)].

Since the A chain was the last chain of laminin for which the entire amino acid sequence was determined, only a few peptides have been described with functional activity. Synthetic peptide PA 21 (residues #1115–1129; cys-gln-ala-gly-thr-phe-ala-leu-arg-gly-asp-asn-pro-gln- gly) (SEQ ID NO:9), which contains the active sequence RGD, induces the attachment of human endothelial cells through an integrin receptor [Grant et al., *Cell*, 58, 933–943 (1989)]. Peptide PA22-2 (residues #2091–2108; ser-arg-ala-arg-lys-gln-ala- ala-ser-ile-lys-val-ala-val-ser-ala-asp-arg) (SEQ ID NO:10), contains the active sequence ile-lys-val-ala-val (SEQ ID NO:11) [Tashiro et al., *J. Biol. Chem.*, 264, 16174–16182 (1989)] and has a number of biological functions such as promoting neuronal process extension [Tashiro et al., supra (1989); Sephel et al., *Biochem. Biophys. Res. Commun.*, 162, 821–829 (1989)]. Recently the biological activity of this peptide has come into question.

The functions that have been described above make laminin an important component of many diverse and clinically important processes such as cell migration, cell adhesion, cell growth, cell differentiation, wound healing, angiogenesis in general, nerve regeneration, tumor cell invasion and metastasis [Liotta, *Am. J. Path.*, 117, 339–348 (1984); McCarthy et al., *Cancer Met. Rev.*, 4, 125–152 (1985)], diabetic microangiopathy, and vascular hypertrophy due to hypertension, atherosclerosis and coronary artery disease, and vessel wall healing after angioplasty. Laminin could also be used in various devices and materials used in humans. In order to better understand the pathophysiology of these processes at the molecular level, it is important to try to assign each of the biological activities that laminin exhibits to a specific subdomain or oligopeptide of laminin. If this can be achieved, potentially important pharmaceuticals based on small peptides or compounds that bind to the receptors producing specific functions of the native, intact molecule, can be synthesized.

Therefore, a need exists to isolate and characterize peptides which are responsible for the wide range of biological activities associated with laminin. Such lower molecular weight oligopeptides would be expected to be more readily obtainable and to exhibit a narrower profile of biological activity than laminin itself, thus increasing their potential usefulness as therapeutic or diagnostic agents.

BRIEF DESCRIPTION OF THE INVENTION

The present invention provides polypeptides which represent fragments of the amino terminal globular domain [domain VI as denoted by Sasaki et al., supra (1988)] (SEQ ID NO:12) of the A chain of laminin. These polypeptides are at least 5 amino acids in length and can be prepared by conventional solid phase peptide synthesis. The formulas of preferred peptides are:

lys-leu-val-glu-his-val-pro-gly-arg-pro-val-arg-his-ala-gln-cys-arg (R17)

arg-pro-val-arg-his-ala-gln-cys-arg-val-cys-asp-gly-asn-ser-thr-asn-pro-arg-glu-arg-his (R18)

arg-tyr-lys-ile-thr-pro-arg-arg-gly-pro-pro-thr-tyr-arg (R19)

ala-arg-tyr-ile-arg-leu-arg-leu-gln-arg-ile-arg-thr-leu (R20)

his-arg-asp-leu-arg-asp-leu-asp-pro-ile-val-thr-arg-arg-tyr-tyr-tyr-ser-ile-lys (R32)

Polypeptide R17 formally represents isolated laminin residues 34–50 from the A chain of laminin; polypeptide R18 formally represents isolated laminin residues 42–63 from the A chain of laminin; polypeptide R19 formally represents isolated laminin residues 145–158 (SEQ ID NO:13); polypeptide R20 formally represents isolated laminin residues 204–217; and polypeptide R32 formally represents isolated laminin residues 226–245 from the deduced sequence of the EHS laminin A chain (SEQ ID NO:14). The single letter amino acid codes for these polypeptides are KLVEHVPGRPVRHAQCR (SEQ ID NO:1) RPVRHAQCRVCDGNSTNPRERH (SEQ ID NO.2), RYKITPRRGPPTYR (SEQ ID NO:3), ARYIRLRLQR-IRTL (SEQ ID NO:4), and HRDLRDLDPIVTRRYYYSIK (SEQ ID NO:5), respectively.

These synthetic polypeptides were assayed for bioactivity and found to be potent promoters of cell adhesion to synthetic substrates. In particular, peptide R18 promoted the adhesion of a variety of cells including: (a) melanoma cells, (b) fibrosarcoma cells, (c) human colon cells, (d) human renal cells, and (e) human keratinocytes. Therefore, it is believed that these polypeptides, among many other things, may be useful to: (a) assist in nerve regeneration, (b) promote wound healing and implant acceptance, (c) promote cellular attachment and growth on culture substrata, and (d) inhibit the metastasis of malignant cells. Due to the difference in the spectra of biological activities exhibited by the polypeptides described herein, mixtures of these peptides are within the scope of the invention.

Furthermore, since it is expected that further digestion/hydrolysis of polypeptides from domain VI of the A chain of laminin in vitro or in vivo will yield fragments of substantially equivalent bioactivity, such lower molecular weight polypeptides are considered to be within the scope of the present invention. For example, while preferred domain VI polypeptides of the A chain of laminin described herein have sequences of at least 14 amino acids, it is to be understood that polypeptides having shorter sequences of amino acids and with functionally active sequences are within the scope of the invention. For example, polypeptides having sequences of fewer than 10 amino acids with functionally active sequences are within the scope of the invention. Further, it is believed that polypeptides having sequences of at least about 5 amino acids with functionally active sequences are within the scope of the invention.

BRIEF DESCRIPTION OF THE DRAWINGS

FIG. 3 reports results in microtiter wells adsorbed with increasing concentrations of HPLC-purified peptides R17 (○) R18 (□), or R19 (△), R20 (●), R32 (■), laminin (▲), or ovalbumin (◇) and radiolabeled HT-1080 human fibrosarcoma cells that were allowed to adhere for 2 hours after being released from flasks with EDTA/trypsin. Each value represents the mean of four separate determinations, and the SEM was less than 10% in each case.

FIG. 11 reports results in microtiter wells absorbed with 0.7 µg of laminin to which cells pre-incubated for 30 minutes in increasing concentrations of HPLC-purified peptide R17 (o) were added and incubated for 30 minutes. Each value represents the mean of four separate determinations and the SEM was less than 10% in each case.

DETAILED DESCRIPTION OF THE INVENTION

Structure of Laminin and the A Chain

Figure 1:
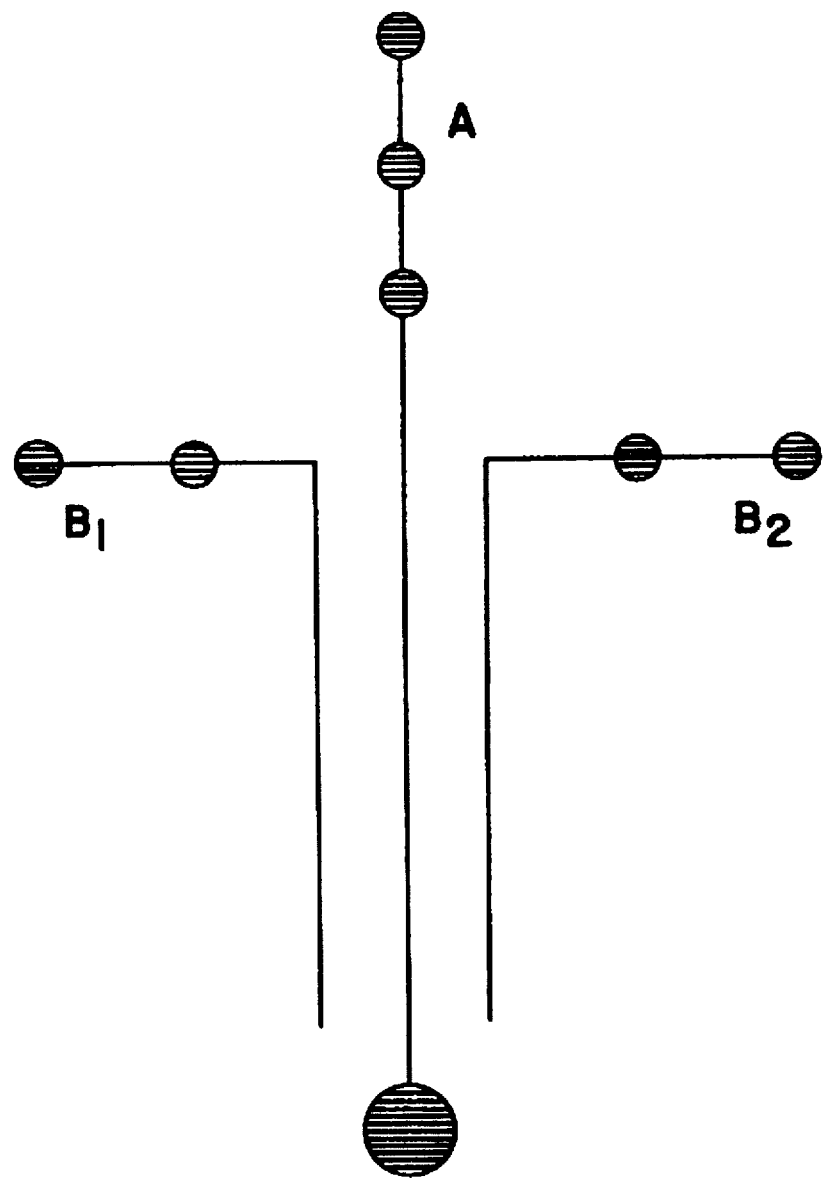
FIG. 1 is a diagrammatic depiction of laminin, indicating the relative location of the A, B1 and B2 chains including globular regions located on each chain.
Figure 2:
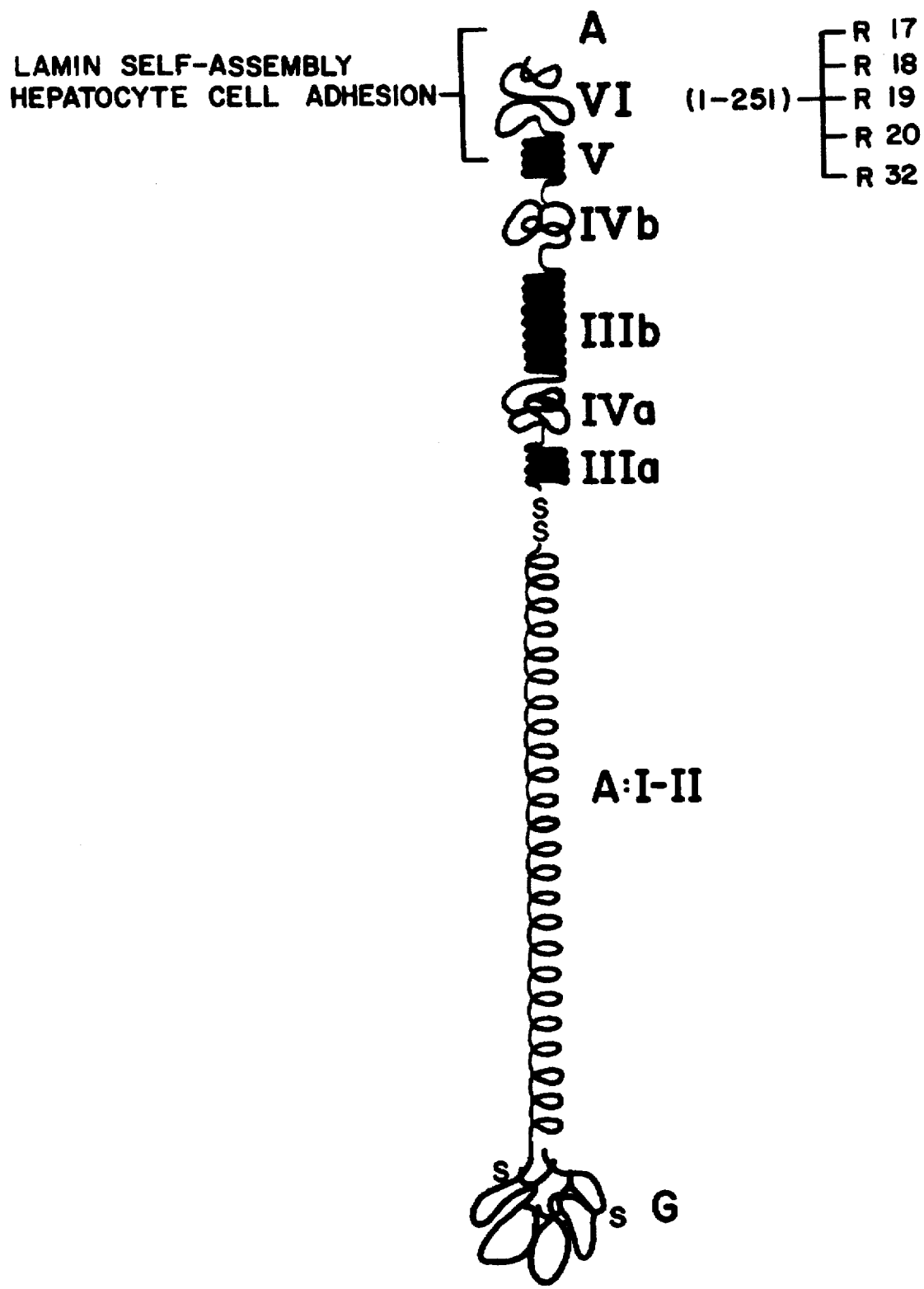
FIG. 2 is a diagrammatic depiction of the A chain of laminin, including domain VI. The location of certain synthetic peptides is shown.

Referring to FIG. 1, when examined by the electron microscope utilizing rotary shadowing techniques, the structure of laminin derived from the mouse EHS tumor appears as an asymmetric cross. The three short arms each have multiple globular domains and are 37 nm in length. The long arm exhibits one large terminal globular domain and is 77 nm in length [Engel et al., supra (1981)]. Laminin likely is one of a multigene family of related molecules [(Ohno et al., supra (1986); Hunter et al., supra. (1989); Sanes et al., supra (1990)]. As seen in FIG. 1, the three chains are associated via disulfide bonds and other chemical bonds. The amino acid sequences of all three polypeptide chains of laminin have now been deduced by sequencing isolated clones having specific laminin genes [Sasaki et al., supra (1988); Sasaki and Yamada, supra (1987); Sasaki et al., *J. Biol. Chem.*, supra (1988)]. Taken together, the three chains are composed of a total of 6,456 amino acids. A diagrammatic model of the A chain is shown in FIG. 2.

In an earlier study, hepatocytes were shown to adhere to a proteolytic resistant fragment of laminin comprised of domain VI [Timpl et al., supra (1983)]. However, the exact amino acid sequence responsible for promoting hepatocyte adhesion is not known and therefore no related oligopeptide has been identified.

Domain VI of laminin does not seem to bind glycosaminoglycans or proteoglycans, as evident by studies which localized heparin binding activity to other sites of laminin (Ott et al., supra (1982); Skubitz et al., supra (1988)].

Therefore, it is likely that cell surface receptors for domain VI of laminin, as well as for these synthetic peptides, are not proteoglycans or glycosaminoglycans. In fact, $^3$H-heparin does not adhere to peptides R17, R18, R19, R20, or R32 in solid-phase binding assays. Perhaps integrins or other cell surface proteins serve as receptors for these peptides. A variety of integrins that bind laminin have been isolated from cells, including $\alpha_1\beta_1$, $\alpha_2\beta_1$, $\alpha_3\beta_1$, $\alpha_6\beta_1$, and $\alpha_v\beta_3$, [Kirchhofer et al., *J. Biol. Chem.*, 265, 615–618 (1990); Kramer et al., *J. Cell Biol.*, 111, 1233–1243 (1990); Gehlsen et al., *J. Biol. Chem.*, 264, 19034–19038 (1989)]. A few of these integrins have been shown to bind to specific regions of laminin. For example, the $\alpha_6\beta_1$ integrin appears to bind to the lower part of the long arm laminin [Sonnenberg et al., *J. Cell Biol.*, 110, 2145–2155 (1990)] whereas $\beta_1$ and $\beta_3$ integrin subunits [Sonnenberg et al., supra (1990)] and the $\alpha_1\beta_1$ integrin from human JAR choriocarcinoma cells bind near the cross region of laminin [Hall et al., *J. Cell Biol.*, 110, 2175–2184 (1990)]. The $\alpha_3\beta_1$ integrin from human MG-63 osteosarcoma cells has been reported to bind near the carboxy terminus of the $B_1$ chain of laminin [Gehlsen et al., supra (1989)]. However, the exact amino acid sequence of laminin to which any of these integrin subunits binds is not known and therefore no related oligopeptide has been identified.

Domain VI of laminin is also important for the self-assembly of laminin into aggregates. Laminin molecules polymerize into large complexes using the globular domains at the ends of the arms [Yurchenco et al., supra (1985)]. The two-step process is temperature-dependent and divalent cation-dependent [Yurchenco et al., supra (1985)]. In particular, the short arms of laminin, including domain VI, are crucial for self-assembly [Schittny and Yurchenco, *J. Cell Biol.*, 110, 825–832 (1990)] and require calcium for self-assembly [Brunch et al., *Eur. J. Biochem.*, 185, 271–279 (1989)]. Laminin self-assembly may be important in maintaining the structure of the basement membrane; perhaps by forming large aggregates, the pore size of a basement membrane can be reduced in order to restrict macromolecular permeation. Furthermore, this process may be important for basement membrane assembly during development and organogenesis [Ekblom, *J. Cell Biol.*, 91, 1–10 (1981)].

According to the present invention, we have investigated domain VI of the A chain of laminin and synthesized a number of peptide fragments with cell attachment promoting activity. We synthesized 5 peptides, each of ~17 amino acid residues in length, from the published amino acid sequence of the amino terminal globular domain of the A chain of laminin [Sasaki et al., supra (1988)]. The polypeptides synthesized and their properties are set forth in Tables I and II, respectively. Peptides R17 and R18 are preferred embodiments of the present invention. Peptides R19, R20, and R32 also have biological activity.

TABLE I

Peptides from the Amino Terminus of Laminin A Chain

| Peptide | Sequence* | Sequence Numbers* | Net Charge+ | Hydropathy Index § |
|---|---|---|---|---|
| R17 | KLVEHVPGR PVRHAQCR (SEQ ID NO: 1) | 34–50 | +5 | −7.8 |
| R18 | RPVRHAQCRV CDGNSTNPRERH (SEQ ID NO: 2) | 42–63 | +5 | −31.0 |

TABLE I-continued

Peptides from the Amino Terminus of Laminin A Chain

| Peptide | Sequence* | Sequence Numbers* | Net Charge+ | Hydropathy Index § |
|---|---|---|---|---|
| R19 | RYKITPRRGPPTYR (SEQ ID NO: 3) | 145–158 | +5 | −20.6 |
| R20 | ARYIRLRLQRIRTL (SEQ ID NO: 4) | 204–217 | +5 | −7.4 |
| R32 | HRDLRDLDPIVT RRYYYSIK (SEQ ID NO: 5) | 226–245 | +3 | −17.0 |

*Based on Sasaki et al. 1988. [G = Glycine; A = Alanine' V = Valine; L = Leucine; I = Isoleucine; F = Phenylalanine; Y = Tyrosine; W = Tryptophan; M = Methionine; C = Cysteine; S = Serine; T = Threonine; H = Histidine; K = Lysine; R = Arginine; D = Aspartate; E = Glutamate; N = Asparagine; Q = Glutamine; P = Proline.]
+Calculated by assuming a +1 net charge for lysine (K) and arginine (R) residues and a −1 net charge for glutamic acid (E) and aspartic acid (D) at neutral pH. Histidine is assumed to be uncharged at this pH.
§Calculated by the method of Kyte and Doolittle (1982). According to this method, more hydrophobic peptides correspond to the more positive numerical values. We constructed hydropathy plots for the entire A chain of laminin using a Sun Computer and an IntelliGenetics (Mountain View, CA) program with a span setting of 6–7 amino acids.

Synthesis of the Polypeptides

The peptides listed in Table I (designated R-series), were derived from the amino terminal globular domain VI (residues #1–251; $M_r$=26,695) of the A chain of EHS laminin. They were synthesized, then HPLC-purified as previously described by Charonis et al., *J. Cell Biol.*, 107, 1253–1260 (1988). Purity was checked by HPLC and amino acid analysis. Specifically, the polypeptides of the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2d ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized by hand or at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract. Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4N methanesulfonic acid, when cysteine or tryptophan are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by amino acid sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

Protein Isolation

Laminin was isolated from the EHS tumor as described by Palm and Furcht, *J. Cell Biol.*, 96, 1218–1226 (1983) with minor modifications. Specifically, tumor tissue was homogenized in 3.4M NaCl, 0.01M phosphate buffer, pH 7.4, with 50 µg/ml of the protease inhibitors PMSF (Sigma Chemical Co., St. Louis, Mo.) and p-hydroxymercuribenzoate (Sigma Chemical Co.), washed twice with the same buffer, then extracted overnight with 0.5M NaCl, 0.01M phosphate, pH 7.4, and 50 µg/ml of the protease inhibitors. The salt concentration was raised to 1.7M followed by stirring overnight at 4° C., then spun at 15,000 rpm for 15 minutes. Laminin was precipitated from the supernatant overnight at 4° C. with 30% saturation ammonium sulfate. The precipitate was resuspended in 0.5M NaCl, 0.01M phosphate, pH 7.4, and dialyzed against the same buffer. Aggregates were removed by ultracentrifugation at 40,000 g for 1 hour at 4° C. Laminin was isolated from the supernatant by gel filtration chromatography on Sephacryl S-300 (Pharmacia Fine Chemicals, Piscataway, N.J.) (2.6×100 cm column) in the 0.5M NaCl buffer, where it eluted just after the void volume. The laminin solution was concentrated by evaporation while in a dialysis bag, dialyzed against PBS and stored at −70° C. The purity of laminin was verified by SDS-PAGE and ELISA. BSA (grade V, fatty acid free) was purchased from Sigma Chemical Co.

The invention will be further described by reference to the following detailed examples.

EXAMPLE 1

Cell Adhesion Assays

Cells

The human fibrosarcoma HT-1080 cell line was obtained from the ATCC. The murine melanoma K-1735-C10 (low metastatic) and K-1735-M4 (high metastatic) cell lines, murine UV-2237-MM fibrosarcoma cell line, human renal carcinoma SN12 PM-6 (high metastatic) cell line, and human colon carcinoma KM12 C (low metastatic) and KM12 SM (high metastatic) cell lines were originally provided by Dr. I. J. Fidler (M.D., Anderson Hospital, University of Texas Health Sciences Center, Houston, Tex.). The MM fibrosarcoma cell line was maintained in DME (GIBCO Laboratories, Grand Island, N.Y.) containing 10% FBS, the murine melanomas were maintained in DMEM containing 10% calf serum, the human fibrosarcoma cells were maintained in EMEM containing 10% heat inactivated FBS, and the human renal and colon carcinoma cells were grown in EMEM containing 10% FBS, vitamins, and 1 mM sodium pyruvate. Cells were passaged for 4 to 5 weeks and then replaced from frozen stocks of early passage cells to minimize phenotypic drift. Cells were maintained at 37° C. in a humidified incubator containing 5% $CO_2$.

Assay Procedure and Results

The direct adhesion of cells to protein or peptide coated surfaces was performed as described in Skubitz et al., Exp. Cell Res., 173, 349–360 (1987) and Charonis et al., supra (1988). Briefly, radiolabeled cells were added to 96-well microtiter plates coated with various concentrations of synthetic peptides, laminin, or BSA (0.02 μg/well–50 μg/well from 50 μl solutions) for various lengths of time. After the incubation period, loosely or nonadherent cells were removed by washing the wells three times. Adherent cells weresolubilized and quantitated in a scintillation counter. More specifically, cultures of cells which were 60–80% confluent were metabolically labeled for 24 hours with the addition of 3 μCi/ml of $^3$H-td (tritiated thymidine). On the day of the assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells were adjusted to a concentration of $3-4\times10^4$/ml, and 100 μl of this cell suspension was added to the wells. The assay mixture was then incubated at 37° C. for 120 minutes. At the end of the incubation, the wells were washed with warm DMEM/Hepes containing 2 mg/ml BSA, and the adherent population was solubilized with 0.5N NaOH contained 1% SDS. The solubilized cells were then quantitated using a liquid scintillation counter.

Figure 3:
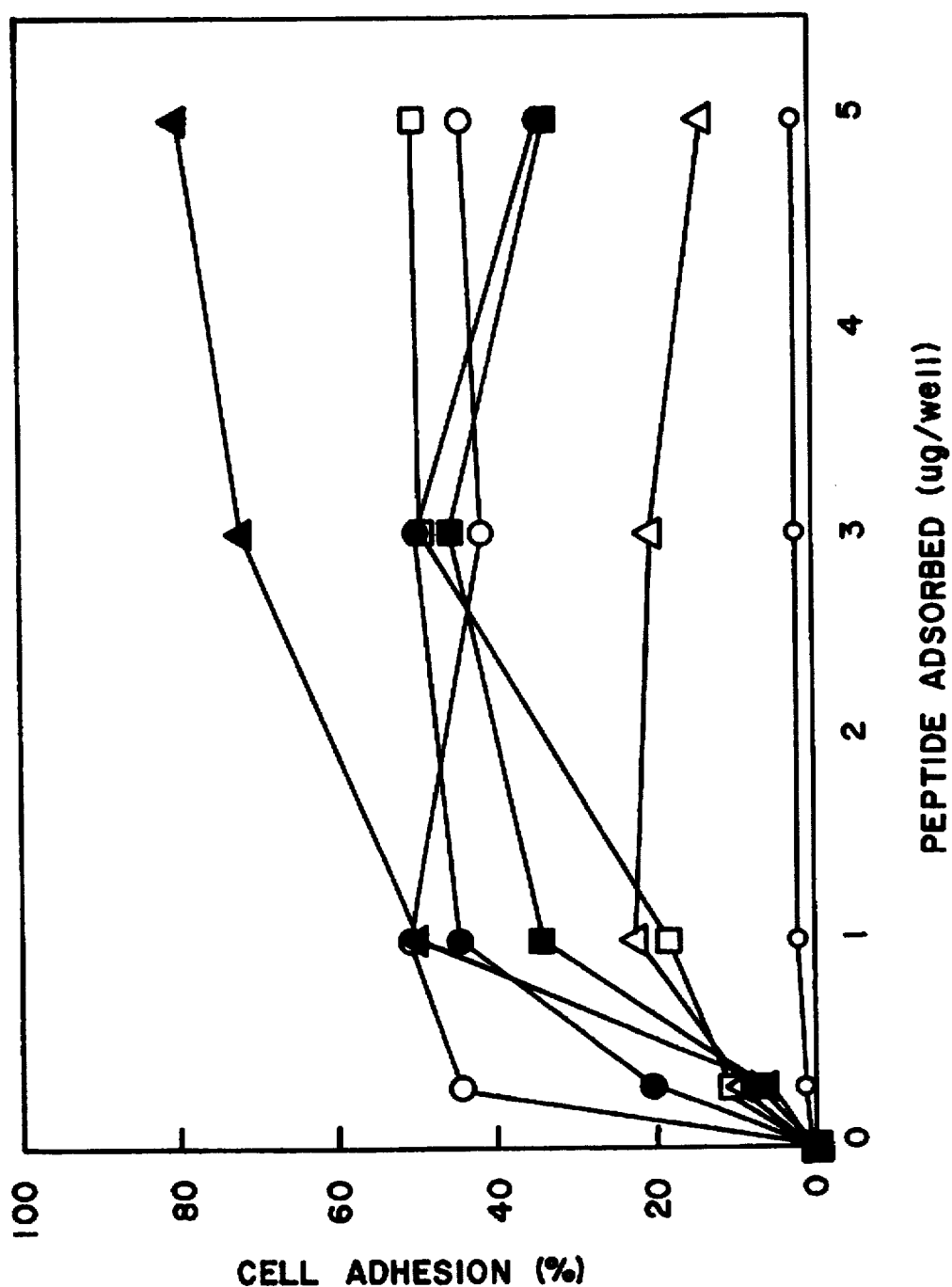
FIG. 3 shows adhesion of HT-1080 human fibrosarcoma cells to laminin A chain peptides.

A representative example of the adhesion of cells to synthetic peptides is shown in FIG. 3. In this case, increasing concentrations of the five synthetic peptides were adsorbed to microtiter wells. Radiolabeled HT-1080 human fibrosarcoma cells were incubated in the wells for 120 minutes and the adhesion of cells was quantitated. Cells adhered to all 5 peptides in a concentration-dependent, saturable manner with maximal cell adhesion of approximately 40% of the total added cells occurring when wells were adsorbed with 3 μg of peptides R17, R18, R20, and R32. Similar patterns of concentration dependence and saturability were observed for peptide R19, however lower levels of cell adhesion were observed. In contrast, no cell adhesion was observed in wells adsorbed with ovalbumin even at concentrations as high as 5 μg/well.

Since peptide R18 promoted the highest levels of HT-1080 fibrosanoma cell adhesion, we decided to focus our studies on this peptide. Microtiter wells were adsorbed with peptide R18, laminin, or BSA and a variety of tumor cell lines were tested for the ability to adhere to the ligands. The six different tumor cell lines selected for this study were of murine or human origin and, in most cases, of either high or low metastatic capacity. As reported in Table II, peptide R18 was also capable of promoting the adhesion of all six cell lines.

TABLE II

Direct Cell Adhesion to Surfaces Coated with Laminin Synthetic Peptide R18

| Cell Line | Cell Adhesion (%)* to Coated Surfaces | | |
|---|---|---|---|
| | Peptide R18 | Laminin | BSA |
| murine melanoma (M4) | 15 | 50 | 3 |
| murine melanoma (C10) | 37 | 80 | 1 |
| murine fibrosarcoma (MM) | 44 | 43 | 1 |
| human colon carcinoma (KI2SM) | 56 | 36 | 2 |
| human colon carcinoma (K12C) | 35 | 25 | 3 |
| human renal carcinoma (SN12 PM6) | 88 | 40 | 1 |

*Microtiter wells were coated with 5 μg of the peptide or proteins and radiolabeled cells were allowed to adhere for 2 hours. Cell adhesion is expressed as a percentage of the total number of cells added to the wells.

EXAMPLE 2

Inhibition of Cell Adhesion to Surfaces Coated with Laminin

Figure 11:
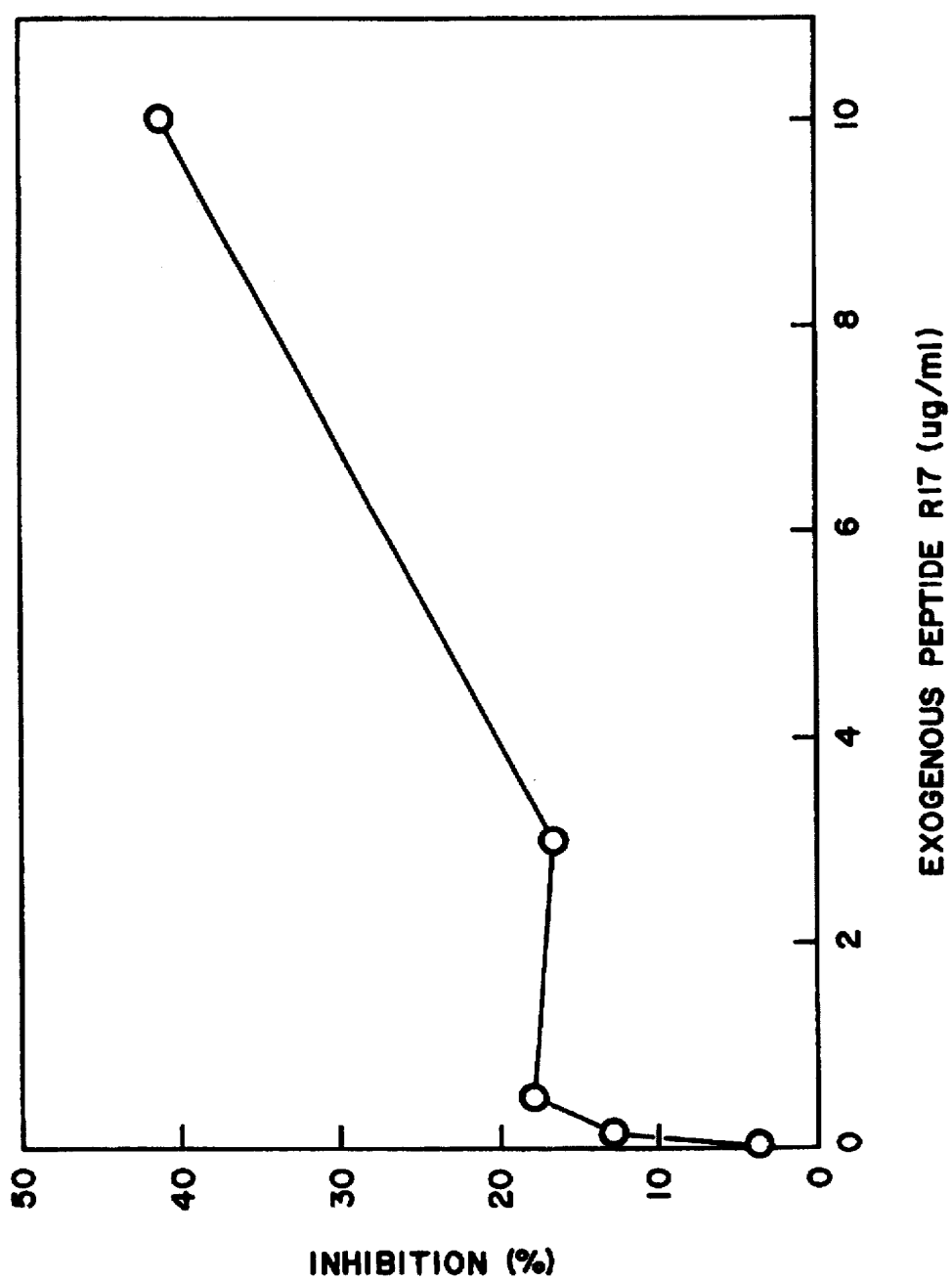
FIG. 11 shows inhibition of laminin-mediated HT-1080 human fibrosarcoma cell adhesion by laminin A chain peptide R11.

Inhibition of cell adhesion with synthetic peptides was performed using assays similar to those described by Skubitz et al., supra (1987). Briefly, radiolabeled cells at $5\times10^4$/ml were incubated for 30 minutes with various concentrations of synthetic peptides (0.05 μg/ml–10 μg/ml) in DME/Hepes containing 2 mg/ml BSA. One hundred microliters of the cell suspension was then added to wells precoated with 0.7 μg of laminin. The cells were incubated for 30 minutes at 37° C., then the wells were washed and adherent cells were quantitated as previously described [Skubitz et al., supra (1987)]. Cell viability after a one hour incubation in the presence of the "inhibitors" was assessed by trypan blue dye exclusion. In all cases, the cells were >95% viable, and no toxicity of the peptides was observed at the indicated concentrations tested. Inhibition of cell adhesion by peptide R17 is reported in FIG. 11.

EXAMPLE 3

Cell Spreading Assay

Spreading of the adherent cells was evaluated by performing adhesion assays similar to those described above. Twenty-four well tissue culture plates (Becton Dickinson and Co., Lincoln Park, N.J.) were coated with 300 μl of laminin, synthetic peptides, or BSA at 100 μg/ml, then blocked with 2 mg/ml BSA in PBS. Three hundred microliters of a cell suspension at $5\times10^4$ cells/ml was added to each well, and after a 2½ hour incubation, nonadherent cells were aspirated out of the wells. Adherent cells were fixed with 2% glutaraldehyde in PBS at 23° C. for one hour. The glutaraldehyde was then removed and the cells were stained by two different techniques. For photographic purposes, the cells were stained with Diff-Quik Solution I (American Scientific Products, McGaw Park, Ill.) for 10 minutes at 23° C. Solution I was removed, then Diff-Quik Solution II was added and the cells were stained for another 10 minutes at 23° C. Wells were washed with PBS, then representative cells were photographed with a Nikon DIAPHOT inverted phase microscope using Panatomic X Film ASA32 (Eastman Kodak, Rochester, N.Y.). Adherent cells to be quantitated for spreading were stained overnight at 23° C. with 500 μl of a solution containing 0.12% (w/v) Coomassie Brilliant Blue R (Sigma Chemical Co.), 5% (v/v) acetic acid, and 50% (v/v) ethanol. Wells were washed three times with 500 µl of PBS and cell spreading was then quantitated by measuring the average surface area occupied by a cell using an Opti-Max Image Analyzer. Thirty cells were measured per well; each experiment was done in quadruplicate and repeated three times. The quantitation of spreading for human HT-1080 fibrosarcoma cells is shown in Table III. Cells spread the best on peptide R17 and R18 and occupy an area of ~30% of that seen for cells on laminin-coated surfaces. On surfaces coated with peptides R19, R20, and R32, less cell spreading was observed; cells occupied an area ~20% of that seen on intact laminin. Cell spreading on ovalbumin (negative control) was less than 10% of that seen on laminin but the cells were barely adherent under these last conditions.

Human HT-1080 fibrosarcoma cell spreading on laminin synthetic peptides from the A chain is shown in FIGS. 4–10. The peptides of most interest to us are those which promoted the most cell spreading (i.e., peptides R17 and R18).

TABLE III

Quantitation of HT-1080 Human Fibrosarcoma Cell Spreading on Surfaces Coated with Laminin A Chain Peptides

| Laminin A Chain Peptide | Surface Area Occupied by a Cell (um$^2$) | Cells Spread (%) |
| --- | --- | --- |
| R17 | 235 ± 58 | 10 |
| R18 | 199 ± 59 | 5 |
| R19 | 129 ± 45 | 5 |
| R20 | 101 ± 34 | 0 |
| R32 | 122 ± 41 | 5 |
| Laminin | 611 ± 79 | 95 |
| Ovalbumin | 71 ± 41 | 0 |

Figure 4:
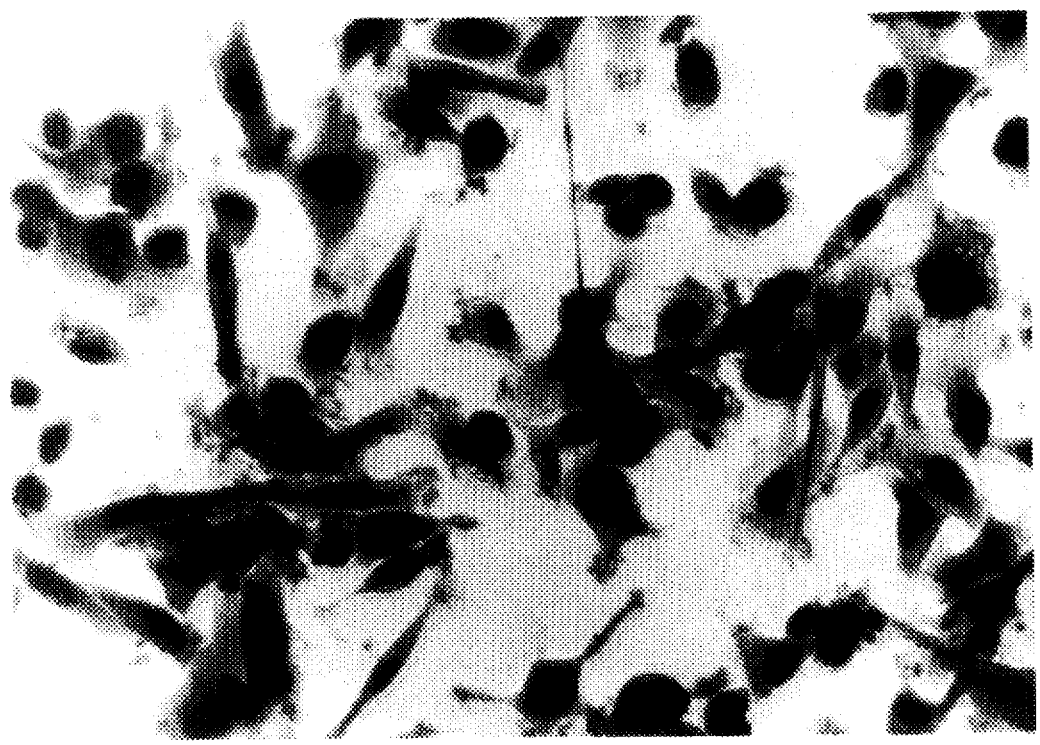
FIG. 4 shows human HT-1080 fibrosarcoma cell spreading on a plastic surface coated with laminin.
Figure 5:
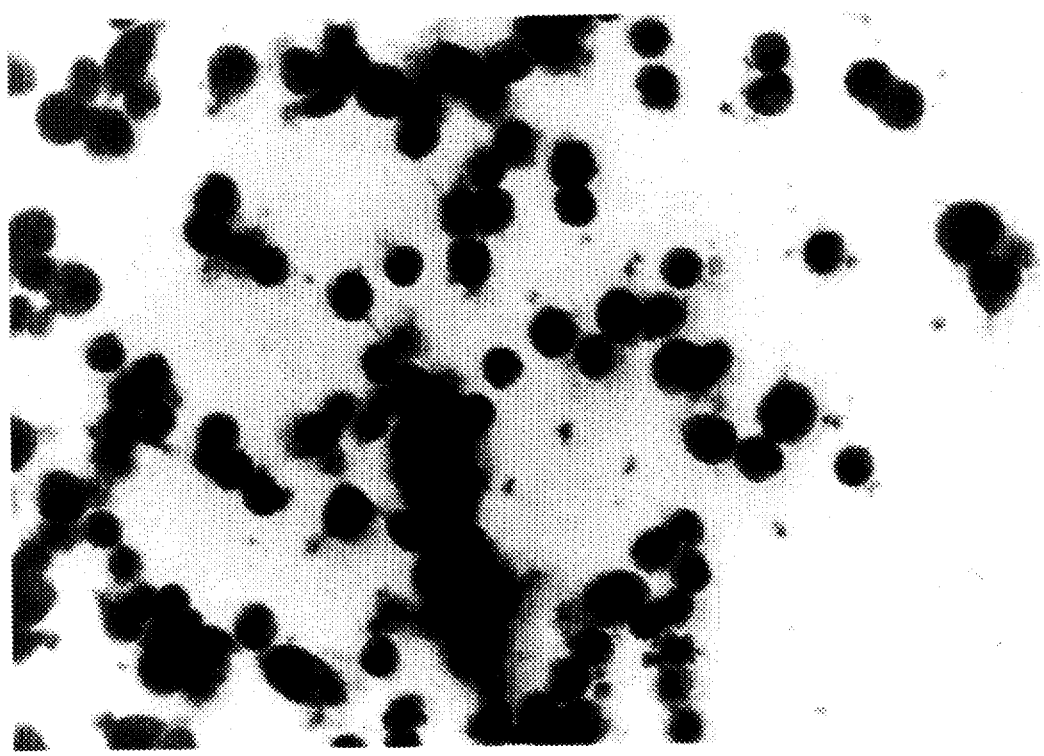
FIG. 5 shows human HT-1080 fibrosarcoma cell spreading on a plastic surface coated with synthetic peptide R17 derived from the A chain of laminin.
Figure 6:
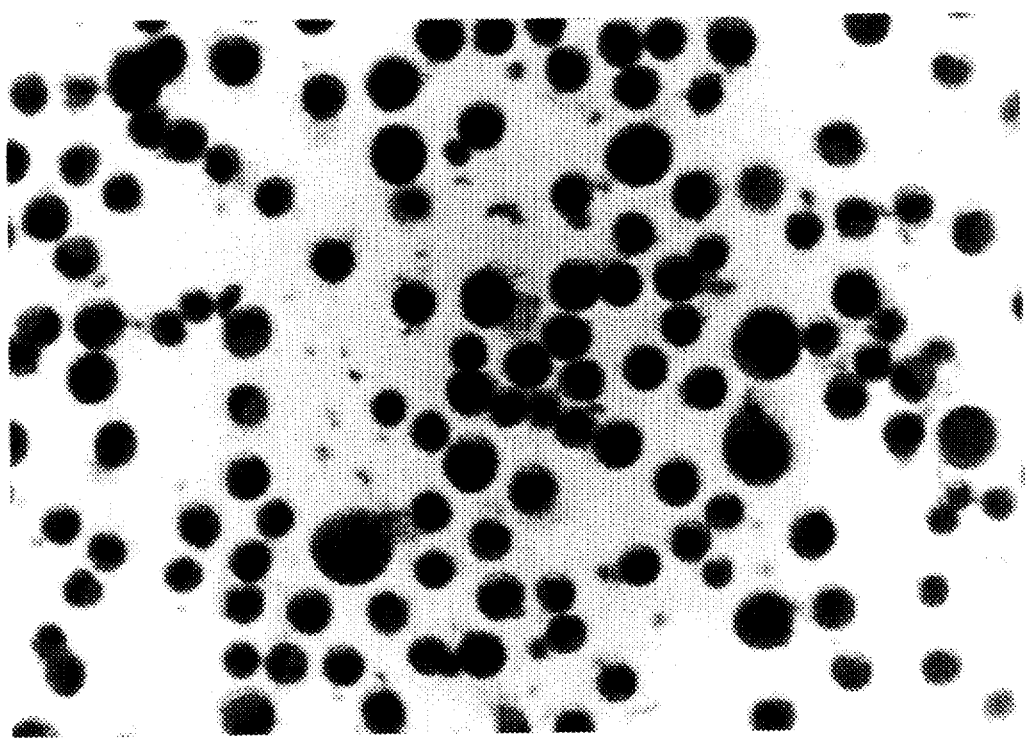
FIG. 6 shows human HT-1080 fibrosarcoma cell spreading on a plastic surface coated with synthetic peptide R18 derived from the A chain of laminin.
Figure 7:
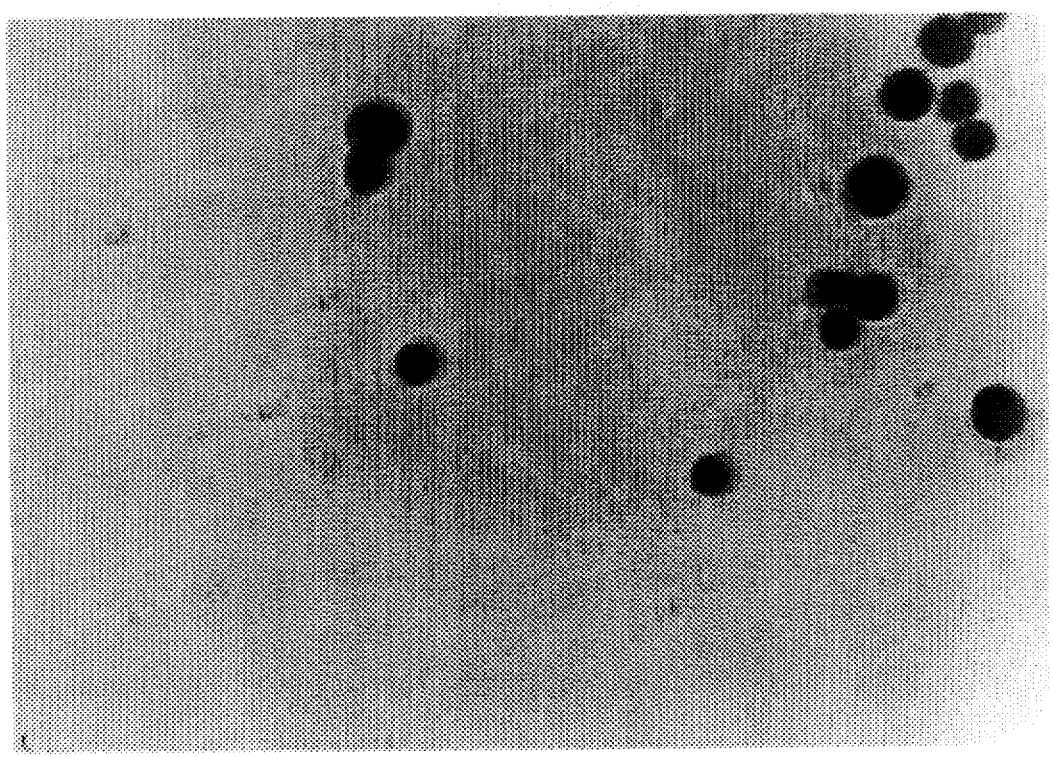
FIG. 7 shows human HT-1080 fibrosarcoma cell spreading on a plastic surface coated with synthetic peptide R19 derived from the A chain of laminin.
Figure 8:
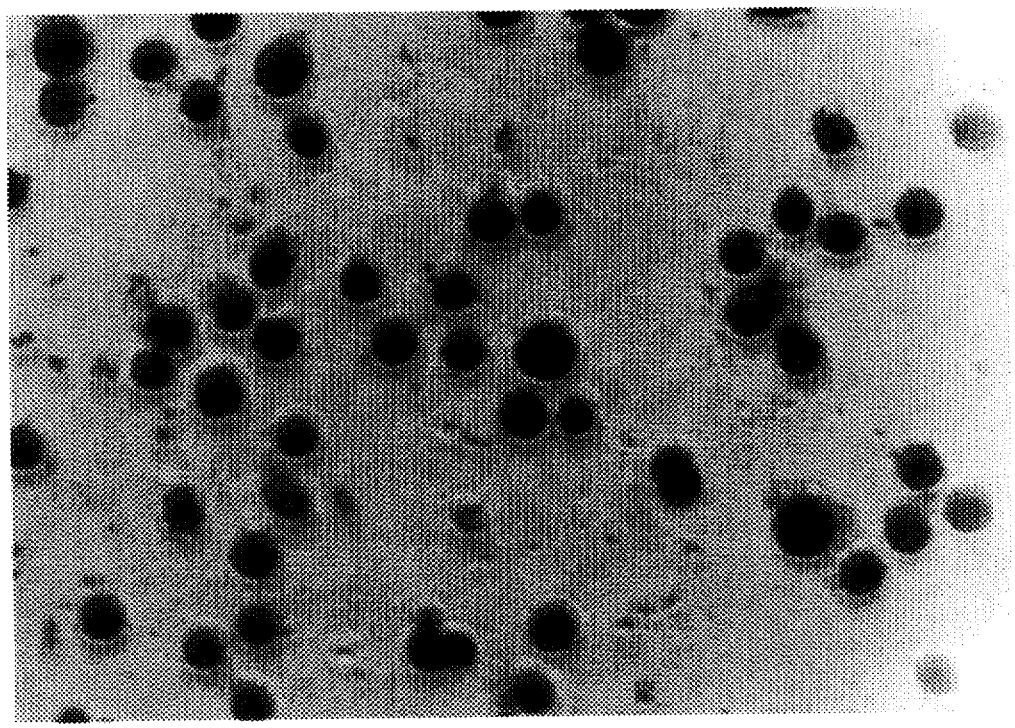
FIG. 8 shows human HT-1080 fibrosarcoma cell spreading on a plastic surface coated with synthetic peptide R20 derived from the A chain of laminin.
Figure 9:
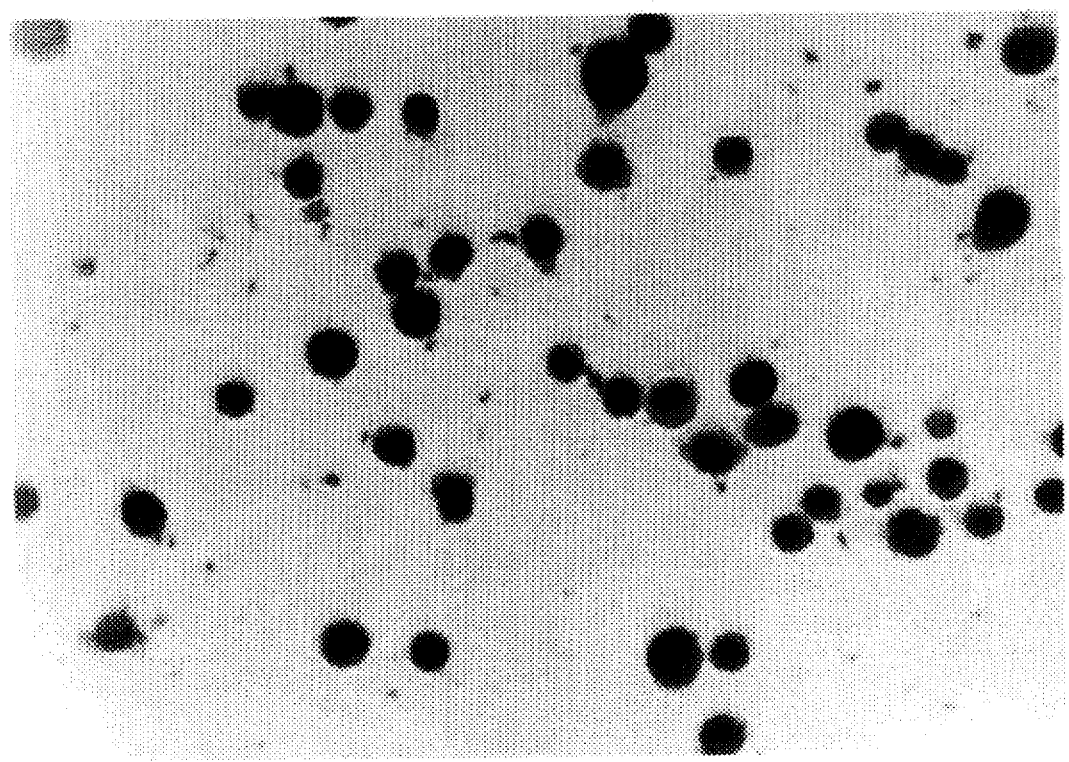
FIG. 9 shows human HT-1080 fibrosarcoma cell spreading on a plastic surface coated with synthetic peptide R32 derived from the A chain of laminin.
Figure 10:
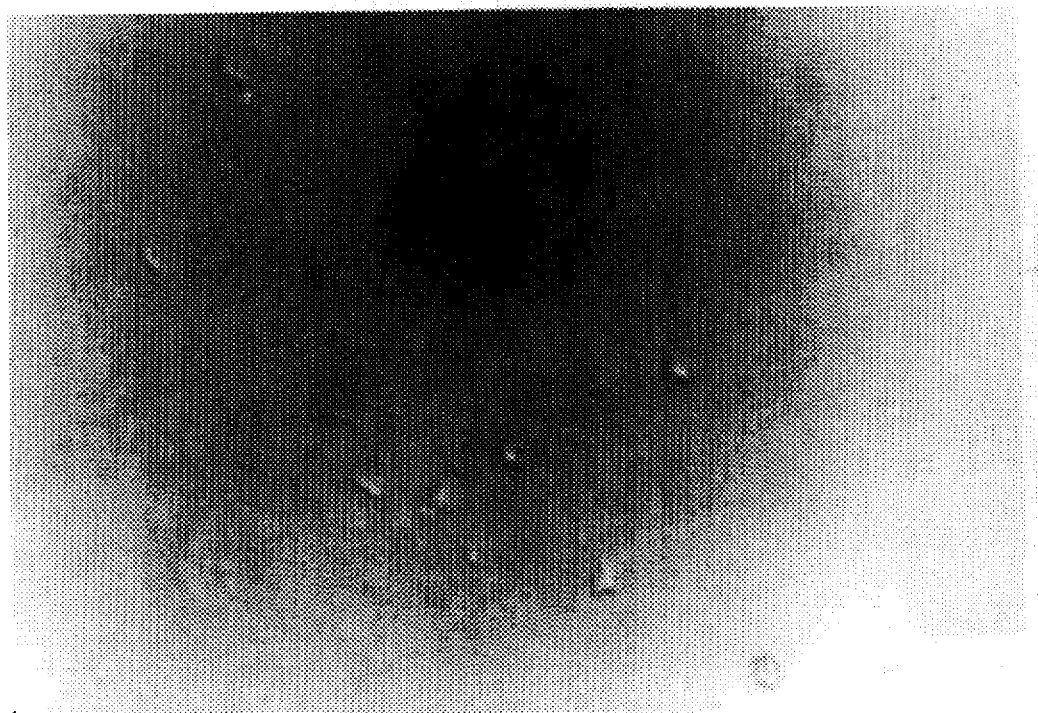
FIG. 10 shows human HT-1080 fibrosarcoma cell spreading on a plastic surface coated with ovalbumin (negative control protein).

FIGS. 4 and 10 provided control comparisons for HT-1080 cell spreading evaluation.

EXAMPLE 4

Heparin Does Not Bind to Plastic Plates Coated with Peptides

The binding of $^3$H-heparin to laminin A chain peptides was measured in a direct solid phase binding assay as described below, whereby various amounts of the peptides were adsorbed to plates and $^3$H-heparin was added to each well. More specifically, the binding of $^3$H-heparin (0.3 mCi/mg; Du Pont - New England Nuclear Research Products, Wilmington, Del.) to laminin, synthetic peptides, and bovine serum albumin (BSA) (fatty acid free, fraction V, ICN Immunobiologicals) was quantitated by a solid-phase RLBA in 96-well polystyrene Immulon 1 plates (Dynatech Laboratories, Inc., Alexandria, Va.) as described by Skubitz et al., supra (1988). Specifically, 50 microliters of the various proteins at various concentrations (0.2 µg/well–5.0 µg/well) in PBS containing 0.02% NaN$_3$ was added to each well and dried overnight at 29° C. The next day, 200 µl of 2 mg/ml BSA in PBS was added to each well, followed by a 2 hour incubation at 37° C. After removal of this buffer, 50 µl of $^3$H-heparin (200,000 dpm) was added in RLBA buffer (20 mM Tris, ,pH 6.8 containing 50 mM NaCl and 2 mg/ml ovalbumin) and the wells were incubated at 37° C. for 2 hours. Unbound $^3$H-heparin was removed by washing three times with wash buffer (RLBA buffer containing 0.1% CHAPS). Tritiated heparin was solubilized by incubation with 200 µl of 0.05N NaOH and 1% SDS for 30 minutes at 60° C. and quantitated in a Beckman LS-3801 scintillation counter. The results indicated that none of the peptides were capable of binding $^3$H-heparin (not shown).

A number of practical applications for the polypeptides of the present invention can be envisioned. Such applications include the promotion of the healing of wounds and modulating the body's response to the placement of synthetic substrata within the body. Such synthetic substrata can include artificial vessels, intraocular contact lenses, hip replacement implants and the like, where modulating cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft, which is generally woven or knitted from nitrocellulose or polyester fiber, particularly Dacron™ (polyethylene terephthalate) fiber. Most types of cells are attracted to laminin and to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush trauma (e.g., spinal cord injuries) or after angioplasty.

In such cases, it may be advantageous to couple the peptide to another biological molecule, such as collagen, a glycosaminoglycan or a proteoglycan. It is also indicative of their value in coating or cross linking to surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs, catheters or infusion pumps.

Laminin can effectively promote the growth and differentiation of diverse Cell types. Also, the polypeptides of the present invention can be used to promote cell adhesion of various cell types to naturally occurring or artificial substrata intended for use in vitro. For example, a culture surface such as the wells of a microtiter plate or the medium contacting surface of microporous fibers or beads, can be coated with the cell-attachment polypeptides.

As one example of commercial use of cell attachment surfaces, Cytodex 3® microcarriers, manufactured by Pharmacia, are dextran-based microspheres coated with denatured collagen, making it possible to grow the same number of adherent cells in a much smaller volume of medium than would be possible in dishes. The activity of these beads is generally dependent upon the use of coating protein in the growth medium and the present polypeptides are expected to provide an improved, chemically-defined coating for such purposes. Other surfaces or materials may be coated to enhance attachment, such as glass, agarose, synthetic resins or long-chain polysaccharides.

In the past, selected laminin domains have been studied for ability to decrease the metastatic potential of invasive cell lines [McCarthy et al., J. Natl. Cancer Inst., 80, 108–116 (1988)]. This effect is mediated via the saturation and therefore neutralization of cell surface receptors for laminin. In accordance with the present invention, the data presented herein suggest that receptors for the polypeptides derived from domain VI of the A chain of laminin should exist on cell surfaces of malignant cells. Consequently, these and related polypeptides could be used to block laminin receptors of metastatic cells and therefore reduce their metastatic potential or spreading.

The invention has been described with reference to various specific and preferred embodiments and techniques. However, it should be understood that many variations and modifications may be made while remaining within the spirit and scope of the invention.

---

What is claimed is:

1. A laminin polypeptide fragment having a sequence of at least five amino acids corresponding substantially to an amino acid sequence from residues 1–158 or residues 204–251 within domain VI of the A chain of laminin, wherein said polypeptide promotes cell adhesion.

* * * * *

UNITED STATES PATENT AND TRADEMARK OFFICE
CERTIFICATE OF CORRECTION

PATENT NO. : 5,703,205

DATED : DECEMBER 30, 1997

INVENTOR(S) : SKUBITZ ET AL.

It is certified that error appears in the above-identified patent and that said Letters Patent is hereby corrected as shown below:

Col. 2, line 3: "supr$_a$" should read —supra—

Col. 2, line 65: "tought" should read —thought—

Col. 11, line 62: delete "," after the word "Tris, "

Col. 12, line 40: "Cell" should read —cell—

Col. 13, sequence 1, line 5: "17" should read —16—

Col. 13, sequence 1, line 9: "peptide" should read —None—

Signed and Sealed this

Twenty-ninth Day of December, 1998

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Lys Leu Val Glu His Val Pro Gly Arg Pro Val Arg His Ala Gln Cys
1               5                   10                  15
Arg ( 2 ) INFORMATION FOR SEQ ID NO:2:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:2:

Arg Pro Val Arg His Ala Gln Cys Arg Val Cys Asp Gly Asn Ser Thr
1               5                   10                  15
Asn Pro Arg Glu Arg His
                20

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:3:

Arg Tyr Lys Ile Thr Pro Arg Arg Gly Pro Pro Thr Tyr Arg
1               5                   10

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:4:

```
Ala  Arg  Tyr  Ile  Arg  Leu  Arg  Leu  Gln  Arg  Ile  Arg  Thr  Leu
 1              5                        10
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:5:

```
His  Arg  Asp  Leu  Arg  Asp  Leu  Asp  Pro  Ile  Val  Thr  Arg  Arg  Tyr  Tyr
 1              5                        10                        15
Tyr  Ser  Ile  Lys
          20
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:6:

```
Cys  Asp  Pro  Gly  Tyr  Ile  Gly  Ser  Arg
 1              5
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:7:

```
Arg  Tyr  Val  Val  Leu  Pro  Arg  Pro  Val  Cys  Phe  Glu  Lys  Gly  Met  Asn
 1              5                        10                        15
Tyr  Thr  Val  Arg
          20
```

( 2 ) INFORMATION FOR SEQ ID NO:8:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: None ( x i ) SEQUENCE DESCRIPTION: SEQ ID NO:8:

```
Arg  Ile  Gln  Asn  Leu  Leu  Lys  Ile  Thr  Asn  Leu  Arg  Ile  Lys  Phe  Val
 1              5                        10                        15
Lys
```

( 2 ) INFORMATION FOR SEQ ID NO:9:

( i ) SEQUENCE CHARACTERISTICS:
        ( A ) LENGTH: 15 amino acids (B) TYPE: amino acid
(C) STRANDEDNESS: single
(D) TOPOLOGY: linear (ii) MOLECULE TYPE: None (xi) SEQUENCE DESCRIPTION: SEQ ID NO:9:

| Cys | Gln | Ala | Gly | Thr | Phe | Ala | Leu | Arg | Gly | Asp | Asn | Pro | Gln | Gly |
|---|---|---|---|---|---|---|---|---|---|---|---|---|---|---|
| 1 | | | | 5 | | | | | 10 | | | | | 15 |

(2) INFORMATION FOR SEQ ID NO:10:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:10:

| Ser | Arg | Ala | Arg | Lys | Gln | Ala | Ala | Ser | Ile | Lys | Val | Ala | Val | Ser | Ala |
|---|---|---|---|---|---|---|---|---|---|---|---|---|---|---|---|
| 1 | | | | 5 | | | | | 10 | | | | | 15 | |

Asp Arg (2) INFORMATION FOR SEQ ID NO:11:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:11:

| Ile | Lys | Val | Ala | Val |
|---|---|---|---|---|
| 1 | | | | 5 |

(2) INFORMATION FOR SEQ ID NO:12:

(i) SEQUENCE CHARACTERISTICS:
(A) LENGTH: 251 amino acids
(B) TYPE: amino acid
(C) STRANDEDNESS: single
(D) TOPOLOGY: linear (ii) MOLECULE TYPE: None (xi) SEQUENCE DESCRIPTION: SEQ ID NO:12:

| Gln | Gln | Arg | Gly | Leu | Phe | Pro | Ala | Ile | Leu | Asn | Leu | Ala | Thr | Asn | Ala |
|---|---|---|---|---|---|---|---|---|---|---|---|---|---|---|---|
| 1 | | | | 5 | | | | | 10 | | | | | 15 | |
| His | Ile | Ser | Ala | Asn | Ala | Thr | Cys | Gly | Glu | Lys | Gly | Pro | Glu | Met | Phe |
| | | | 20 | | | | 25 | | | | | 30 | | | |
| Cys | Lys | Leu | Val | Glu | His | Val | Pro | Gly | Arg | Pro | Val | Arg | His | Ala | Gln |
| | | 35 | | | | | 40 | | | | | 45 | | | |
| Cys | Arg | Val | Cys | Asp | Gly | Asn | Ser | Thr | Asn | Pro | Arg | Glu | Arg | His | Pro |
| | | 50 | | | | | 55 | | | | 60 | | | | |
| Ile | Ser | His | Ala | Ile | Asp | Gly | Thr | Asn | Asn | Trp | Trp | Gln | Ser | Pro | Ser |
| 65 | | | | | 70 | | | | | 75 | | | | | 80 |
| Ile | Gln | Asn | Gly | Arg | Glu | Tyr | His | Trp | Val | Thr | Val | Thr | Leu | Asp | Leu |
| | | | | 85 | | | | | 90 | | | | | 95 | |
| Arg | Gln | Val | Phe | Gln | Val | Ala | Tyr | Ile | Ile | Ile | Lys | Ala | Ala | Asn | Ala |
| | | | | 100 | | | | | 105 | | | | 110 | | |
| Pro | Arg | Pro | Gly | Asn | Trp | Ile | Leu | Glu | Arg | Ser | Val | Asp | Gly | Val | Lys |

|     |     |     |     | 115 |     |     |     |     | 120 |     |     |     |     | 125 |     |
|-----|-----|-----|-----|-----|-----|-----|-----|-----|-----|-----|-----|-----|-----|-----|-----|

Phe Lys Pro Trp Gln Tyr Tyr Ala Val Ser Asp Thr Glu Cys Leu Thr
130                     135                     140

Arg Tyr Lys Ile Thr Pro Arg Arg Gly Pro Pro Thr Tyr Arg Ala Asp
145                 150                 155                 160

Asn Glu Val Ile Cys Thr Ser Tyr Tyr Ser Lys Leu Val Pro Leu Glu
                165                 170                 175

His Gly Glu Ile His Thr Ser Leu Ile Asn Gly Arg Pro Ser Ala Asp
            180                 185                 190

Asp Pro Ser Pro Gln Leu Leu Glu Phe Thr Ser Ala Arg Tyr Ile Arg
        195                 200                 205

Leu Arg Leu Gln Arg Ile Arg Thr Leu Asn Ala Asp Leu Met Thr Leu
    210                 215                 220

Ser His Arg Asp Leu Arg Asp Leu Asp Pro Ile Val Thr Arg Arg Tyr
225                 230                 235                 240

Tyr Tyr Ser Ile Lys Asp Ile Ser Val Gly Gly
            245                 250

(2) INFORMATION FOR SEQ ID NO:13:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

Gln Gln Arg Gly Leu Phe Pro Ala Ile Leu Asn Leu Ala Thr Asn Ala
1               5                   10                  15

His Ile Ser Ala Asn Ala Thr Cys Gly Glu Lys Gly Pro Glu Met Phe
            20                  25                  30

Cys Lys Leu Val Glu His Val Pro Gly Arg Pro Val Arg His Ala Gln
        35                  40                  45

Cys Arg Val Cys Asp Gly Asn Ser Thr Asn Pro Arg Glu Arg His Pro
    50                  55                  60

Ile Ser His Ala Ile Asp Gly Thr Asn Asn Trp Trp Gln Ser Pro Ser
65                  70                  75                  80

Ile Gln Asn Gly Arg Glu Tyr His Trp Val Thr Val Thr Leu Asp Leu
                85                  90                  95

Arg Gln Val Phe Gln Val Ala Tyr Ile Ile Ile Lys Ala Ala Asn Ala
            100                 105                 110

Pro Arg Pro Gly Asn Trp Ile Leu Glu Arg Ser Val Asp Gly Val Lys
        115                 120                 125

Phe Lys Pro Trp Gln Tyr Tyr Ala Val Ser Asp Thr Glu Cys Leu Thr
130                     135                     140

Arg Tyr Lys Ile Thr Pro Arg Arg Gly Pro Pro Thr Tyr Arg
145                 150                 155

(2) INFORMATION FOR SEQ ID NO:14:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: None ( x i ) SEQUENCE DESCRIPTION: SEQ ID NO:14:

```
Ala Arg Tyr Ile Arg Leu Arg Leu Gln Arg Ile Arg Thr Leu Asn Ala
 1               5                  10                      15

Asp Leu Met Thr Leu Ser His Arg Asp Leu Arg Asp Leu Asp Pro Ile
            20                  25              30

Val Thr Arg Arg Tyr Tyr Tyr Ser Ile Lys Asp Ile Ser Val Gly Gly
        35                  40                  45
```